(12) United States Patent
Ashurst et al.

(10) Patent No.: US 6,532,955 B1
(45) Date of Patent: *Mar. 18, 2003

(54) METERED DOSE INHALER FOR ALBUTEROL

(75) Inventors: Ian C. Ashurst, Ware (GB); Ignatius Loy Britto, Cary, NC (US); Craig Steven Herman, Raleigh, NC (US); Li Li-Bovet, Chapel Hill, NC (US); Michael Thomas Riebe, Raleigh, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/570,789

(22) Filed: May 15, 2000

Related U.S. Application Data

(63) Continuation of application No. 08/831,268, filed on Mar. 31, 1997, now Pat. No. 6,131,566, which is a continuation-in-part of application No. 08/584,860, filed on Jan. 5, 1996, now abandoned, which is a continuation-in-part of application No. 08/422,371, filed on Apr. 14, 1995, now abandoned, said application No. 08/831,268, is a continuation of application No. PCT/US96/05002, filed on Apr. 10, 1996, which is a continuation-in-part of application No. 08/584,860, filed on Jan. 5, 1996, now abandoned, which is a continuation-in-part of application No. 08/422,371, filed on Apr. 14, 1995, now abandoned.

(51) Int. Cl.$^7$ ............................................. A61M 11/00

(52) U.S. Cl. ............................ 128/200.23; 128/200.14

(58) Field of Search ...................... 128/200.14, 200.22, 128/200.23, 203.12

(56) References Cited

U.S. PATENT DOCUMENTS

| | | | |
|---|---|---|---|
| 2,562,118 A | | 7/1951 | Osdal |
| 2,721,010 A | | 10/1955 | Meshberg |
| 2,886,217 A | | 5/1959 | Thiel |
| 2,892,576 A | | 6/1959 | Ward |
| 2,968,427 A | | 1/1961 | Meshberg |
| 2,980,301 A | | 4/1961 | de Gorter |
| 3,049,269 A | | 8/1962 | Gawthrop |
| 3,052,382 A | | 9/1962 | Gawthrop |
| 3,506,737 A | | 4/1970 | Smith et al. |
| 3,611,990 A | | 10/1971 | Paoletti et al. |
| 3,644,353 A | * | 2/1972 | Lunts et al. ............... 544/162 |
| 3,739,950 A | * | 6/1973 | Gorman ................. 128/200.23 |
| 3,896,602 A | | 7/1975 | Petterson |
| 3,929,537 A | | 12/1975 | Erwin |
| 3,962,171 A | | 6/1976 | Robbins |
| 4,087,026 A | | 5/1978 | Petterson |
| 4,125,152 A | | 11/1978 | Kestner et al. |
| 4,143,204 A | | 3/1979 | Fang |
| 4,180,609 A | | 12/1979 | Vassiliou |
| 4,335,121 A | * | 6/1982 | Phillipps et al. ............. 424/241 |
| 4,339,483 A | | 7/1982 | Ueno et al. |
| 4,407,481 A | | 10/1983 | Bolton et al. |
| 4,423,823 A | | 1/1984 | Franek et al. |
| 4,626,157 A | | 12/1986 | Franek et al. |
| 4,678,106 A | * | 7/1987 | Newell et al. ......... 128/200.23 |
| 4,741,934 A | | 5/1988 | Terayama et al. |
| 4,819,834 A | | 4/1989 | Thiel |
| 4,826,132 A | | 5/1989 | Moldenhauer |
| 4,861,647 A | | 8/1989 | Ishikawa et al. |
| 4,897,439 A | | 1/1990 | Rau et al. |
| 4,902,318 A | | 2/1990 | Stevens et al. |
| 4,945,008 A | | 7/1990 | Heyes et al. |
| 4,961,966 A | | 10/1990 | Stevens et al. |
| 4,969,577 A | | 11/1990 | Werding |
| 4,980,210 A | | 12/1990 | Heyes |
| 4,992,474 A | | 2/1991 | Skidmore et al. |

(List continued on next page.)

FOREIGN PATENT DOCUMENTS

| | | |
|---|---|---|
| AU | 0012188 | 9/1992 |
| CA | 2130867 | 8/1994 |
| DE | 2252754 | 10/1972 |

(List continued on next page.)

OTHER PUBLICATIONS

G. Bukton, *International J. Pharm.*, 83, 163–170 (1992).
*Journal of Teflon*, 4, pp. 1 and 4–6 (1963).
*Journal of Teflon*, 1, pp. 1 and 7 (1960).
Encyc. of Polymer Science and Eng., 16, 577–600 (1989).
Kunstoff–Handbuch, Band XI, Section 4.3.6.2 (1971).
Kirk–Othmer Encyc. of Chem. Technology, 11, 1–49 (1980).
Byron, Respiratory Drug Delivery, CRC Press, Inc., FL, 167–201 (1990).
Budavari, The Merck Index, Eleventh Ed., Merck & Co., Inc., pp. 37, 158–159 and 663–664 (1989).
Henry, The British Medical Assoc. Guide to Medicines & Drugs, Dorling Kindersley, London, p. 137 (1992).
L. Lachman et al., *Pharmaceutical Aerosols*, The Theory and Practice of Industrial Pharmacy, Chapter 20, pp. 589–618 (1989).
R. Dalby et al., *Pharmaceutical Technology*, pp. 26–33, Mar. 1990.
*Chemistry and Industry*, p. 347, Jun. 6, 1988.
A. R. Gennaro, *Remington's Pharmaceutical Sciences*, Mack Publishing Co., Inc., pp. 1670–1677 (1985).
Fundamentals of Polymer Adhesion, Chapter VIII, "Adhesion of Polymers to Substrates of an Inorganic Nature", pp. 289–230, 1974 (with English Translation).

*Primary Examiner*—Aaron J. Lewis
(74) *Attorney, Agent, or Firm*—Birch, Stewart. Kolasch & Birch, LLP

(57) ABSTRACT

A metered dose inhaler having all or part of its internal surfaces coated with one or more fluorocarbon polymers, optimally in combination with one or more non-fluorocarbon polymers, for dispensing an inhalation drug formation comprising fluticasone propionate or a physiologically acceptable solvate thereof and a fluorocarbon propellant, optionally in combination with one or more other pharmacologically active agents or one or more excipients.

26 Claims, No Drawings

U.S. PATENT DOCUMENTS

| | | | |
|---|---|---|---|
| 5,006,383 A | | 4/1991 | Achille et al. |
| 5,009,959 A | * | 4/1991 | Matsushita et al. ......... 428/419 |
| 5,043,191 A | | 8/1991 | Endres et al. |
| 5,061,140 A | | 10/1991 | Hamaguchi et al. |
| 5,168,107 A | | 12/1992 | Tennenbaum |
| 5,176,132 A | | 1/1993 | Drought et al. |
| 5,202,110 A | | 4/1993 | Dalby et al. |
| 5,208,226 A | | 5/1993 | Palmer |
| 5,221,576 A | | 6/1993 | Bosc et al. |
| 5,225,183 A | | 7/1993 | Purewal et al. |
| 5,261,538 A | | 11/1993 | Evans et al. |
| 5,270,305 A | | 12/1993 | Palmer |
| 5,340,463 A | | 8/1994 | Layre et al. |
| 5,345,980 A | * | 9/1994 | Burt et al. ...................... 141/3 |
| 5,363,842 A | * | 11/1994 | Mishelevich et al. .. 128/200.23 |
| 5,376,359 A | | 12/1994 | Johnson |
| 5,421,492 A | | 6/1995 | Barger et al. |
| 5,437,267 A | * | 8/1995 | Weinstein .............. 128/200.23 |
| 5,468,798 A | | 11/1995 | Leech |
| 5,503,144 A | | 4/1996 | Bacon |
| 5,508,023 A | | 4/1996 | Byron et al. |
| 5,536,583 A | | 7/1996 | Roberts et al. |
| 5,597,433 A | | 1/1997 | Dyble et al. |
| 5,657,748 A | * | 8/1997 | Braithwaite ............ 128/203.21 |
| 5,674,472 A | | 10/1997 | Akehurst et al. |
| 5,674,473 A | | 10/1997 | Burewal et al. |
| 5,674,592 A | | 10/1997 | Clark et al. |
| 5,676,929 A | | 10/1997 | Akehurst et al. |
| 5,681,545 A | | 10/1997 | Purewal et al. |
| 5,683,676 A | | 11/1997 | Akehurst et al. |
| 5,683,677 A | | 11/1997 | Purewal et al. |
| 5,695,743 A | | 12/1997 | Purewal et al. |
| 5,720,940 A | | 2/1998 | Purewal et al. |
| 6,131,566 A | * | 10/2000 | Ashurst et al. ......... 128/200.14 |
| 6,143,277 A | * | 11/2000 | Ashurst et al. ......... 128/203.15 |

FOREIGN PATENT DOCUMENTS

| | | |
|---|---|---|
| DE | 2252754 A | 5/1973 |
| DE | 2227142 A | 12/1973 |
| DE | 3619926 | 6/1986 |
| DE | 3619926 A1 | 1/1987 |
| DE | 4009397 | 3/1990 |
| DE | 4023909 | 7/1990 |
| DE | 4124730 C2 | 1/1993 |
| EP | 0273980 | 7/1988 |
| EP | 0297712 | 1/1989 |
| EP | 0317865 | 5/1989 |
| EP | 0335315 A1 | 10/1989 |
| EP | 0338670 A2 | 10/1989 |
| EP | 0372777 | 6/1990 |
| EP | 0384606 | 8/1990 |
| EP | 0499142 | 2/1991 |
| EP | 0465741 | 1/1992 |
| EP | 0487200 | 5/1992 |
| EP | 0504112 A2 | 9/1992 |
| EP | 0561981 B1 | 9/1993 |
| EP | 0561987 B1 | 9/1993 |
| EP | 0609453 | 8/1994 |
| EP | 642992 A2 * | 8/1994 |
| EP | 0642992 | 3/1995 |
| FR | 2267496 A | 11/1975 |
| GB | 1322084 | 3/1970 |
| GB | 1191700 | 5/1970 |
| GB | 1362495 | 8/1971 |
| GB | 1392192 | 4/1975 |
| GB | 1394327 | 5/1975 |
| GB | 1588463 | 8/1976 |
| GB | 2003415 | 8/1978 |
| GB | 2003415 | 3/1979 |
| GB | 2105189 | 3/1983 |
| GB | 2214891 | 9/1989 |
| GB | 2216794 | 10/1989 |
| HU | 0168483 | 5/1976 |
| HU | 0196904 | 2/1989 |
| HU | 0208398 | 10/1993 |
| HU | 0209609 | 5/1994 |
| HU | 0196303 | 11/1998 |
| JP | 01009158 | 1/1989 |
| JP | 01214433 | 8/1989 |
| JP | 02067374 | 3/1990 |
| JP | 03093525 | 1/1991 |
| JP | 3199699 | 8/1991 |
| JP | 04353442 | 12/1992 |
| JP | 06142799 | 5/1994 |
| RU | 2008939 | 3/1994 |
| RU | 2012362 | 5/1994 |
| RU | 2027448 | 1/1995 |
| WO | WO8101375 | 5/1981 |
| WO | 8604233 | 7/1986 |
| WO | 9104011 A1 | 4/1991 |
| WO | 9110606 | 7/1991 |
| WO | WO 92/08446 * | 5/1992 |
| WO | WO9208446 | 5/1992 |
| WO | 9208446 | 5/1992 |
| WO | 9211190 | 7/1992 |
| WO | 9220391 | 11/1992 |
| WO | 9311743 | 6/1993 |
| WO | 9311744 A1 | 6/1993 |
| WO | WO 93/11745 * | 6/1993 |
| WO | 9311745 A1 | 6/1993 |
| WO | WO9403153 | 2/1994 |
| WO | 9400921 | 6/1994 |
| WO | 9422722 | 10/1994 |
| WO | WO 96/32151 * | 10/1996 |

* cited by examiner

METERED DOSE INHALER FOR ALBUTEROL

This application is a continuation of U.S. application Ser. No. 08/831,268 filed on Mar. 31, 1997 (now U.S. Pat. No. 6,131,566, which issued on Oct. 17, 2000), which is a continuation-in-part of application Ser. No. 08/584,860 filed on Jan. 5, 1996 (now abandoned), which is a continuation-in-part of application Ser. No. 08/422,371 filed on Apr. 14, 1995 (now abandoned). Application Ser. No. 08/831,268 is also a continuation of PCT International Application No. PCT/US96/05002 filed Apr. 10, 1996, which designated the United States, which is a continuation-in-part of application Ser. No. 08/584,860 filed on Jan. 5, 1996 (now abandoned), which is a continuation-in-part of application Ser. No. 08/422,371 filed on Apr. 14, 1995 (now abandoned). The entire contents of each of the above-identified applications are hereby incorporated by reference.

BACKGROUND OF THE INVENTION

Drugs for treating respiratory and nasal disorders are frequently administered in aerosol formulations through the mouth or nose. One widely used method for dispensing such aerosol drug formulations involves making a suspension formulation of the drug as a finely divided powder in a liquefied gas known as a propellant. The suspension is stored in a sealed container capable of withstanding the pressure required to maintain the propellant as a liquid. The suspension is dispersed by activation of a dose metering valve affixed to the container.

A metering valve may be designed to consistently release a fixed, predetermined mass of the, drug formulation upon each activation. As the suspension is forced from the container through the dose metering valve by the high vapor pressure of the propellant, the propellant rapidly vaporizes leaving a fast moving cloud of very fine particles of the drug formulation. This cloud of particles is directed into the nose or mouth of the patient by a channelling device such as a cylinder or open-ended cone. Concurrently with the activation of the aerosol dose metering valve, the patient inhales the drug particles into the lungs or nasal cavity. Systems of dispensing drugs in this way are known as "metered dose inhalers" (MDI's). See Peter Byron, Respiratory Drug Delivery, CRC Press, Boca Raton, Fla. (1990) for a general background on this form of therapy.

Patients often rely on medication delivered by MDI's for rapid treatment of respiratory disorders which are debilitating and in some cases, even life threatening. Therefore, it is essential that the prescribed dose of aerosol medication delivered to the patient consistently meet the specifications claimed by the manufacturer and comply with the requirements of the FDA and other regulatory authorities. That is, every dose in the can must be the same within close tolerances.

Some aerosol drugs tend to adhere to the inner surfaces, i.e., walls of the can, valves, and caps, of the MDI. This can lead to the patient getting significantly less than the prescribed amount of drug upon each activation of the MDI. The problem is particularly acute with hydrofluoroalkane (also known as simply "fluorocarbon") propellant systems, e.g., P134a and P227, under development in recent years to replace chlorofluorocarbons such as P11, P114 and P12.

We have found that coating the interior can surfaces of MDI's with a fluorocarbon polymer significantly reduces or essentially eliminates the problem of adhesion or deposition of albuterol on the can walls and thus ensures consistent delivery of medication in aerosol form the MDI.

SUMMARY OF THE INVENTION

A metered dose inhaler having part or all of its internal surfaces coated with one or more fluorocarbon polymers, optionally in combination with one or more non-fluorocarbon polymers, for dispensing an inhalation drug formulation comprising albuterol, or a physiologically acceptable salt thereof, and a fluorocarbon propellant, optionally in combination with one or more other pharmacologically active agents or one or more excipients.

DETAILED DESCRIPTION OF THE INVENTION

The term "metered dose inhaler" or "MDI" means a unit comprising a can a crimped cap covering the mouth of the can, and a drug metering valve situated in the cap, while the term "MDI" system also includes a suitable channelling device. The terms "MDI can" means the container without the cap and valve. The term "drug metering valve" or "MDI valve" refers to a valve and its associated mechanisms which delivers a predetermined amount of drug formulation from an MDI upon each activation. The channelling device may comprise, for example, an actuating device for the valve and a cylindrical or cone-like passage through which medicament may be delivered from the filled MDI can via the MDI valve to the nose or mouth of a patient, e.g. a mouthpiece actuator. The relation of the parts of a typical MDI is illustrated in U.S. Pat. No. 5,261,538 incorporated herein by reference.

The term "fluorocarbon polymers" means a polymer in which one or more of the hydrogen atoms of the hydrocarbon chain have been replaced by fluorine atoms.

Thus, "fluorocarbon polymers" include perfluorocarbon, hydrofluorocarbon, chlorofluorocarbon, hydrochlorofluorocarbon polymers or other halogen substituted derivatives thereof. The "fluorocarbon polymers" may be branched, homo-polymers or co-polymers.

U.S. Pat. No. 3,644,363, incorporated herein by reference, teaches a group of bronchodilating compounds that are particularly useful in the treatment of asthma and other respiratory diseases. The preferred compound taught therein is $\alpha^1$-tert-butylaminomethyl-4-hydroxy-m-xylene-$\alpha^1$, $\alpha^3$-diol also known in the US by its generic name "albuterol" and, in most other countries as "salbutamol". Albuterol as the free base and as acid addition salts (particularly as the sulfate salt), especially in aerosol form, has been widely accepted by the medical community in the treatment of asthma and is marketed under such trademarks as "Ventolin" and "Proventil".

The term "drug formulations" means albuterol or a physiologically acceptable salt thereof (particularly the sulfate salt) optionally in combination with one or more other pharmacologically active agents such as antiinflammatory agents, analgesic agents or other respiratory drugs and optionally containing one or more excipients. The term "excipients" as used herein means chemical agents having little or no pharmacological activity (for the quantities used) but which enhance the drug formulation or the performance of the MDI system. For example, excipients include but are not limited to surfactants, preservatives, flavorings, antioxidants, antiaggregating agents, and cosolvents, e.g., ethanol and diethyl ether. Albuterol or salt thereof may be used in the form of its R-isomer.

Suitable surfactants are generally known in the art, for example, those surfactants disclosed in European Patent application No. 0327777. The amount of surfactant employed is desirable in the range of 0.0001% to 50% weight to weight ratio relative to the drug, in particular, 0.05 to 5% weight to weight ratio. A particularly useful surfactant is 1,2-di[7-(F-hexyl) hexanoyl]-glycero-3-phospho-N,N,N-trimethylethanolamine also known as 3,5,9-trioxa-4-phosphadocosan-1-aminium, 17,17,18,18,19,19,20,20,21, 21,22,22,22-tridecafluoro-7-[(8,8, 9,9,10,10,11,11,12,12,13, 13,13-tridecafluoro-1-oxotridecyl)oxy]-4-hydroxy-N,N,N-trimethyl-10-oxo-, inner salt, 4-oxide.

A polar cosolvent such as $C_{2-6}$ aliphatic alcohols and polyols e.g. ethanol, isopropanol and propylene glycol, preferably ethanol, may be included in the drug formulation in the desired amount, either as the only excipient or in addition to other excipients such as surfactants. Suitably, the drug formulation may contain 0.01 to 5% w/w based on the propellant of a polar cosolvent e.g. ethanol, preferably 0.1 to 5% w/w e.g. about 0.1 to 1% w/w.

It will be appreciated by those skilled in the art that the drug formulation for use in the invention may, if desired, contain albuterol or a salt thereof (e.g. the sulphate) in combination with one or more other pharmacologically active agents. Such medicaments may be selected from any suitable drug useful in inhalation therapy. Appropriate medicaments may thus be selected from, for example, analgesics, e.g. codeine, dihydromorphine, ergotamine, fentanyl or morphine; anginal preparations, e.g. diltiazem; antiallergics, e.g. cromoglycate, ketotifen or nedocromil; antiinfectives e.g. cephalosporins, penicillins, streptomycin, sulphonamides, tetracyclines and pentamidine; antihistamines, e.g. methapyrilene; anti-inflammatories, e.g. beclomethasone (e.g. the dipropionate), flunisolide, budesonide, tipredane or triamcinolone acetonide; antitussives, e.g. noscapine; bronchodilators, e.g. salbutamol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, orciprenaline, or (−)-4-amino-3,5-dichloro-α-[[[6-[2-(2-pyridinyl)ethoxy]hexyl]amino]methyl] benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimise the activity and/or stability of the medicament and/or to minimise the solubility of the medicament in the propellant.

Particularly preferred drug formulations contain albuterol or a physiologically acceptable salt thereof in combination with an anti-inflammatory steroid such as fluticasone propionate or beclomethasone dipropionate or physiologically acceptable solvates thereof.

A particularly preferred drug combination is albuterol sulfate and beclomethasone dipropionate.

"Propellants" used herein mean pharmacologically inert liquids with boiling points from about room temperature (25° C.) to about −25° C. which singly or in combination exert a high vapor pressure at room temperature. Upon activation of the MDI system, the high vapor pressure of the propellant in the MDI forces a metered amount of drug formulation out through the metering valve, Then the propellant very rapidly vaporizes dispersing the drug particles. The propellants used in the present invention are low boiling fluorocarbons; in particular, 1,1,1,2-tetrafluoroethane also known as "propellant 134a" or "P 134a" and 1,1,1,2,3,3,3-heptafluoropropane also known as "propellant 227" or "P 227". Preferably, however, the MDI cans employed in the present invention are made of aluminium or an alloy thereof.

Drug formulations for use in the invention may be free or substantially free of formulation excipients e.g. surfactants and cosolvents etc. Such drug formulations are advantageous since they may be substantially taste and odour free, less irritant and less toxic than excipient-containing formulations. Thus, a preferred drug formulation consists essentially of albuterol or a physiologically acceptable salt thereof, optionally in combination with one or more other pharmacologically active agents particularly salmeterol (e.g. in the form of the xinafoate salt), and a fluorocarbon propellant. Preferred propellants are 1,1,1,2-tetrafluoroethane, 1,1,1,2,3,3,3-heptafluoro-n-propane or mixtures thereof, and especially 1,1,1,2-tetrafluoroethane.

Further drug formulations for use in the invention may be free or substantially free of surfactant. Thus, a further preferred drug formulation comprises or consists essentially of albuterol (or a physiologically acceptable salt thereof), optionally in combination with one or more other pharmacologically active agents, a fluorocarbon propellant and 0.01 to 5% w/w based on the propellant of a polar cosolvent, which formulation is substantially free of surfactant. Preferred propellants are 1,1,1,2-tetrafluoroethane, 1,1,1,2,3,3, 3-heptafluoro-n-propane or mixtures thereof, and especially 1,1,1,2-tetrafluoroethane or 1,1,1,2,3,3,3-heptafluoro-n-propane.

Most often the MDI can and cap are made of aluminum or an alloy of aluminum, although other metals not affected by the drug formulation, such as stainless steel, an alloy of copper, or tin plate, may be used. An MDI can may also be fabricated from glass or plastic. Preferably, however, the MDI cans employed in the present invention are made of aluminium or an alloy thereof. Advantageously, strengthened aluminium or aluminum alloy MDI cans may be employed. Such strengthened MDI cans are capable of withstanding particularly stressful coating and curing conditions, e.g. particularly high temperatures, which may be required for certain fluorocarbon polymers. Strengthened MDI cans which have a reduced tendency to malform under high temperatures include MDI cans comprising side walls and a base of increased thickness and MDI cans comprising a substantially ellipsoidal base (which increases the angle between the side walls and the base of the can), rather than the hemispherical base of standard MDI cans. MDI cans having an ellipsoidal base offer the further advantage of facilitating the coating process.

Fluorocarbon polymers for use in the invention include fluorocarbon polymers which are made of multiples of one or more of the following monomeric units; tetrafluoroethylene (PTFE), fluorinated ethylene propylene (FEP), perfluoroalkoxyalkane (PFA), ethylene terafluoroethylene (ETFE), vinyldienefluoride (PVDF), and chlorinated ethylene tetrafluoroethylene. Fluorinated polymers which have a relatively high ratio of fluorine to carbon, such as perfluorocarbon polymers, e.g., PTFE, PFA, and FEP are preferred.

The fluorinated polymer may be blended with non-fluorinated polymers such as polyamides, polyimides, polyethersulfones, polyphenylene sulfides, and amineformaldehyde thermosetting resins. These added polymers improve adhesion of the polymer coating to the can walls. Preferred polymer blends are PTFE/FEP/polyamideimide, PTFE/polyether sulphone (PES) and FEP-benzoguanamine.

Preferably, the fluorocarbon polymers for use in the invention are coated onto MDI cans made of metal, especially MDI cans made of aluminium or an alloy thereof.

Particularly preferred coatings are pure PFA and blends of PTFE and polyethersulphone (PES).

Fluorocarbon polymers are marketed under trademarks such as Teflon®, Tefzel®, Halar® and Hostaflon®, Polyflon® and Neoflon®. Grades of polymer include FEP DuPont 856-200, PFA DuPont 857-200, PTFE-PES DuPont 3200-100, PTFE-FEP-polyamideimide DuPont 856P23485, FEP powder DuPont 532, and PFA Hoechst 6900n. The coating thickness is in the range of about 1 $\mu$m to about 1 mm. Suitably the coating thickness is in the range of about 1 $\mu$m to about 100 $\mu$m, e.g. 1 $\mu$m to 25 $\mu$m. Coatings may be applied in one or more coats The particle size of the particular (e.g., micronised) drug should be such as to permit inhalation of substantially all the drug into the lungs upon administration of the aerosol formulation and will thus be less than 100 microns, desirably less than 20 microns, and, in particular, in the range of 1–10 microns, e.g., 1–5 microns.

The final aerosol formulation desirably contains 0.005–10% weight to weight ratio, in particular 0.005–5% weight to weight ratio, especially 0.01–1.0% weight to weight ratio, of drug relative to the total weight of the formulation.

A further aspect of the present invention is a metered dose inhaler having part or all of its internal metallic surfaces coated with one or more fluorocarbon polymers, optionally in combination with one or more non-fluorocarbon polymers, for dispensing an inhalation drug formulation comprising albuterol or a salt thereof and a fluorocarbon propellant optionally in combination with one or more other pharmacologically active agents and one or more excipients.

A particular aspect of the present invention is an MDI having essentially all of its internal metallic surfaces coated with PFA or FEP, or blended fluoropolymer resin systems such as PTFE-PES with or without a primer coat of a polyamideimide or polyethersulfone for dispensing a drug formulation defined hereinabove.

Preferred drug formulations for use in this MDI consist essentially of albuterol (or a physiologically acceptable salt thereof, e.g. the sulfate), optionally in combination with one or more other pharmacologically active agents particularly beclomethasone dipropionate (or a solvate thereof), and a fluorocarbon propellant, particularly 1,1,1,2-tetrafluoroethane, 1,1,1,2,3,3,3-heptafluoropropane or mixtures thereof, and especially 1,1,1,2-tetrafluoroethane. Preferably the MDI can is made of aluminium or an alloy thereof.

The MDI can may be coated by the means known in the art of metal coating. For example, a metal, such as aluminum or stainless steel, may be precoated as coil stock and cured before being stamped or drawn into the can shape. This method is well suited to high volume production for two reasons. First, the art of coating coil stock well developed and several manufacturers can custom coat metal coil stock to high standards of uniformity and in a wide range of thicknesses. Second, the precoated stock can be stamped or drawn at high speeds and precision by essentially the same methods used to draw or stamp uncoated stock.

Other techniques for obtaining coated cans is by electrostatic dry powder coating or by spraying preformed MDI cans inside with formulations of the coating fluorinated polymer/polymer blend and then curing. The preformed MDI cans may also be dipped in the fluorocarbon polymer/polymer blend coating formulation and cured, thus becoming coated on the inside and out. The fluorocarbon polymer/polymer blend formulation may also be poured inside the MDI cans then drained out leaving the insides with the polymer coat. Conveniently, for ease of manufacture, preformed MDI cans are spray-coated with the fluorinated polymer/polymer blend.

The fluorocarbon polymer/polymer blend may also be formed in situ at the can walls using plasma polymerization of the fluorocarbon monomers. Fluorocarbon polymer film may be blown inside the MDI cans to form bags. A variety of fluorocarbon polymers such as ETFE, FEP, and PTFE are available as film stock.

The appropriate curing temperature is dependent on the fluorocarbon polymer/polymer blend chosen for the coating and the coating method employed.

However, for coil coating and spray coating temperatures in excess of the melting point of the polymer are typically required, for example, about 50° C. above the melting point for up to about 20 minutes such as about 5 to 10 minutes e.g. about 8 minutes or as required. For the above named preferred and particularly preferred fluorocarbon polymer/polymer blends curing temperatures in the range of about 300° C. to about 400° C., e.g. about 350° C. to 380° C. are suitable. For plasma polymerization typically temperatures in the range of about 20° C. to about 100° C. may be employed.

The MDI's taught herein may be prepared by methods of the art (e.g., see Byron, above and U.S. Pat. No. 5,345,980) substituting conventional cans for those coated with a fluorinated polymer/polymer blend. That is, albuterol or a salt thereof and other components of the formulation are filled into an aerosol can coated with a fluorinated polymer/polymer blend. The can is fitted with a cap assembly which is crimped in place. The suspension of the drug in the fluorocarbon propellant in liquid form may be introduced through the metering valve as taught in U.S. Pat. No. 5,345,980 incorporated herein by reference.

The MDI's with fluorocarbon polymer/polymer blend coated interiors taught herein may be used in medical practice in a similar manner as non-coated MDI's now in clinical use. However the MDI's taught herein are particularly useful for containing and dispensing inhaled drug formulations with hydrofluoroalkane fluorocarbon propellants such as 134a with little, or essentially no excipient and which tend to deposit or cling to the interior walls and parts of the MDI system. In certain cases it is advantageous to dispense an inhalation drug with essentially no excipient, e.g., where the patient may be allergic to an excipient or the drug reacts with an excipient.

MDI's containing the formulations described hereinabove, MDI systems and the use of such MDI systems for the treatment of respiratory disorders e.g. asthma comprise further aspects of the present invention.

It will be apparent to those skilled in the art that modifications to the invention described herein can readily be made without departing from the spirit of the invention. Protection is sought for all the subject matter described herein including any such modifications.

The following non-limitative Examples serve to illustrate the invention.

EXAMPLES

Example 1

Standard 12.5 ml MDI cans (Presspart Inc., Cary, N.C.) were spray-coated (Livingstone Coatings, Charlotte, N.C.)

with primer (DuPont 851-204) and cured to the vendor's standard procedure, then further spray-coated with either FEP or PFA (DuPont 856-200 and 857-200, respectively) and cured according to the vendor's standard procedure. The thickness of the coating is approximately 10 μm to 50 μm. These cans are then purged of air (see PCT application number WO94/22722 (PCT/EP94/00921)), the valves crimped in place, and a suspension of about 29 mg albuterol sulfate in about 18.2 gm P134a is filled through the valve.

Example 2

Standard 0.46 mm thick aluminum sheet (United Aluminum) was spray-coated (DuPont, Wilmington, Del.) with FEP (DuPont 856-200) and cured. The thickness of the coating is approximately 10 μm to 50 μm. This sheet was then deep-drawn into cans (Presspart Inc., Cary, N.C.). These cans are then purged of air, the valves crimped in place, and a suspension of about 12 mg albuterol sulfate in about 7.5 gm P134A is filled through the valve.

Example 3

Standard 12.5 ml MDI cans (Presspart Inc., Cary, N.C.) are spray-coated with PTFE-PES blend (DuPont) as a single coat and cured according to the vendor's standard procedure. The thickness of the coating is between approximately 1 μm and approximately 20 μm. These cans are then purged of air, the valves crimped in place, and a suspension of about 31.8 mg or about 15.4 mg micronised albuterol sulphate in about 19.8 g or about 9.6 g respectively P134a is filled through the valve.

Example 4

Standard 12.5 ml MDI cans (Presspart Inc., Cary, N.C.) are spray-coated with PTFE-FEP-polyamideimide blend (DuPont) and cured according to the vendor's standard procedure. The thickness of the coating is between approximately 1 μm and approximately 20 μm. These cans are then purged of air, the valves crimped in place, and a suspension of about 31.8 mg or about 15.4 mg micronised albuterol sulphate in about 19.8 g or about 9.6g respectively P134a is filled through the valve.

Example 5

Standard 12.5 ml MDI cans (Presspart Inc., Cary, N.C.) are spray-coated with FEP powder (DuPont FEP 532) using an electrostatic gun. The thickness of the coating is between approximately 1 μm and approximately 20 μm. These cans are then purged of air, the valves crimped in place, and a suspension of about 31.8 mg or about 15.4 mg micronised albuterol sulphate in about 19.8 g or about 9.6 g respectively P134a is filled through the valve.

Example 6

Standard 0.46 mm thick aluminium sheet (United Aluminium) is spray coated with FEP-Benzoguanamine and cured. This sheet is then deep-drawn into cans. These cans are then purged of air, the valves crimped in place, and a suspension of about 31.8 mg or about 15.4 mg micronised albuterol sulphate in about 19.8 g or about 9.6 g respectively P134a is filled through the valve.

Example 7

Standard 12.5 ml MDI cans (Presspart Inc., Cary, N.C.) are spray-coated with an aqueous dispersion of PFA (Hoechst PFA-6900n) and cured. The thickness of the coating is between approximately 1 μm and approximately 20 μm. These cans are then purged of air, the valves crimped in place, and a suspension of about 31.8 mg or about 15.4 mg micronised albuterol sulphate in about 19.8 g or about 9.6 g respectively P134a is filled through the valve.

Example 8

Standard 12.5 ml MDI cans (Presspart Inc., Cary, N.C.) are spray-coated with PTFE-PES blend (DuPont) as a single coat and cured according to the vendor's standard procedure. The thickness of the coating is between approximately 1 μm and approximately 20 μm. These cans are then purged of air, the valves crimped in place, and a suspension of about 28.9 mg micronised albuterol sulphate in about 18 g P134a is filled through the valve.

Example 9

Standard 12.5 ml MDI cans (Presspart Inc., Cary, N.C.) are spray-coated with PTFE-FEP-polyamideimide blend (DuPont) and cured according to the vendor's standard procedure. The thickness of the coating is between approximately 1 μm and approximately 20 μm. These cans are then purged of air, the valves crimped in place, and a suspension of about 28.9 mg micronised albuterol sulphate in about 18 g P134a is filled through the valve.

Example 10

Standard 12.5 ml MDI cans (Presspart Inc., Cary, N.C.) are spray-coated with FEP powder (DuPont FEP 532) using an electrostatic gun. The thickness of the coating is between approximately 1 μm and approximately 20 μm. These cans are then purged of air, the valves crimped in place, and a suspension of about 28.9 mg micronised albuterol sulphate in about 18 g P134a is filled through the valve.

Example 11

Standard 0.46 mm thick aluminium sheet (United Aluminium) is spray coated with FEP-Benzoguanamine and cured. This sheet is then deep-drawn into cans.

These cans are then purged of air, the valves crimped in place, and a suspension of about 28.9 mg micronised albuterol sulphate in about 18 g P134a is filled through the valve.

Example 12

Standard 12.5 ml MDI cans (Presspart Inc., Cary, N.C.) are spray-coated with an aqueous dispersion of PFA (Hoechst PFA-6900n) and cured. The thickness of the coating is between approximately 1pm and approximately 20 μm. These cans are then purged of air, the valves crimped in place, and a suspension of about 28.9 mg micronised albuterol sulphate in about 18 g P134a is filled through the valve.

Examples 13 to 17

Examples 3 to 7 were repeated except that a suspension of 29 mg micronised albuterol sulphate in about 21.4 g P227 is filled through the valve.

Examples 18 to 22

Examples 3 to 7 were repeated except that 24 mg or 15 mg micronised albuterol sulphate in about 364 mg or 182 mg ethanol respectively and about 18.2 g P134a is filled through the valve.

Examples 23 to 42

Examples 3 to 22 are repeated except that modified 12.5 ml MDI cans having a substantially ellipsoid base (Presspart Inc. Cary NC) are used.

Dose delivery from the MDIs tested under simulated use conditions is found to be constant, compared to control MDIs filled into uncoated cans which exhibit a significant decrease in dose delivered through use.

We claim:

1. A metered dose inhaler having part or all of its internal surfaces coated with one or more fluorocarbon polymers, optionally in combination with one or more non-fluorocarbon polymers, for dispensing an inhalation drug formulation, comprising a particulate drug and a fluorocarbon propellant, optionally in combination with one or more other pharmacologically active agents or one or more excipients.

2. An inhaler according to claim 1, containing said inhalation drug formulation, wherein said drug formulation comprises albuterol or a physiologically acceptable salt thereof.

3. An inhaler according to claim 2, wherein said drug formulation further comprises a surfactant.

4. An inhaler according to claim 2, wherein said drug formulation further comprises a polar cosolvent.

5. An inhaler according to claim 2 wherein said drug formulation comprises 0.01 to 5% w/w based upon propellant of a polar cosolvent, which formulation is substantially free of surfactant.

6. An inhaler according to claim 2, wherein said drug formulation comprises albuterol or a physiologically acceptable salt thereof in combination with an anti-inflammatory steroid or an antiallergic.

7. An inhaler according to claim 6, wherein said drug formulation comprises albuterol or a physiologically acceptable salt thereof in combination with beclomethasone dipropionate or a physiologically acceptable solvate thereof.

8. An inhaler according to claim 2, wherein said drug formulation consists essentially of albuterol or a physiologically acceptable salt thereof, optionally in combination with one or more other pharmacologically active agents, and a fluorocarbon propellant.

9. An inhaler according to claim 8, wherein said drug formulation consists essentially of albuterol or a physiologically acceptable salt thereof in combination with an anti-inflammatory steroid or an antiallergic.

10. An inhaler according to claim 9, wherein said drug formulation consists essentially of albuterol or a physiologically acceptable salt thereof in combination with beclomethasone dipropionate or a physiologically acceptable solvate thereof.

11. An inhaler according to claim 2, wherein said drug formulation consists of albuterol or a physiologically acceptable salt thereof and a fluorocarbon propellant.

12. An inhaler according to claim 2, wherein said albuterol is in the form of the sulfate salt.

13. An inhaler according to claim 2, wherein the fluorocarbon propellant is 1,1,1,2-tetrafluoroethane, or 1,1,1,2,3,3,3-heptafluoro-n-propane or mixtures thereof.

14. An inhaler according to claim 13, wherein the fluorocarbon propellant is 1,1,1,2-tetrafluoroethane.

15. An inhaler according to claim 1, comprising a can made of metal wherein part or all of the internal metallic surfaces are coated.

16. An inhaler according to claim 15 wherein the metal is aluminium or an alloy thereof.

17. An inhaler according to claim 1, wherein said fluorocarbon polymer is a perfluorocarbon polymer.

18. An inhaler according to claim 17, wherein said fluorocarbon polymer is selected from PTFE, PFA, FEP and mixtures thereof.

19. An inhaler according to claim 1, wherein said fluorocarbon polymer is in combination with a non-fluorocarbon polymer selected from polyamideimide and polyethersulphone.

20. A metered dose inhaler system comprising a metered dose inhaler according to claim 1 fitted into suitable channelling device for oral or nasal inhalation of the drug formulation.

21. A method for the treatment of a respiratory disorder, comprising:

administering to a patient by oral or nasal inhalation a drug formulation by using the metered dose inhaler system of claim 20.

22. An inhaler according to claim 1, wherein part or all of the internal surfaces are coated with one or more fluorocarbon polymers in combination with one or more non-fluorocarbon polymers.

23. An inhaler according to claim 1, which contains a drug formulation comprising a particulate drug and fluorocarbon propellant.

24. An inhaler according to claim 23, wherein said propellant comprises 1,1,1,2-tetrafluoroethane.

25. An inhaler according to claim 23, wherein said propellant comprises 1,1,1,2,3,3,3-heptafluoro-n-propane.

26. A metered dose inhaler having part or all of its internal surfaces coated with one or more fluorocarbon polymers, optionally in combination with one or more non-fluorocarbon polymers, for dispensing an inhalation drug formulation, comprising particulate albuterol and a fluorocarbon propellant selected from the group consisting of 1,1,1,2-tetrafluoroethane, 1,1,1,2,3,3,3-heptafluoro-n-propane, and mixtures thereof, optionally in combination with one or more other pharmacologically active agents or one or more excipients.

* * * * *